(12) United States Patent
Lee et al.

(10) Patent No.: US 8,440,649 B2
(45) Date of Patent: May 14, 2013

(54) PHENANTHROINDOLIZIDINE ANALOGUES

(75) Inventors: Shiow-Ju Lee, Tainan (TW);
Cheng-Wei Yang, Kaohsiung (TW);
Yue-Zhi Lee, Tainan (TW)

(73) Assignee: National Health Research Institutes, Miaoli County (TW)

( * ) Notice: Subject to any disclaimer, the term of this patent is extended or adjusted under 35 U.S.C. 154(b) by 456 days.

(21) Appl. No.: 12/703,905

(22) Filed: Feb. 11, 2010

(65) Prior Publication Data

US 2010/0216773 A1 Aug. 26, 2010

Related U.S. Application Data

(60) Provisional application No. 61/154,825, filed on Feb. 24, 2009, provisional application No. 61/154,826, filed on Feb. 24, 2009.

(51) Int. Cl.
*A01N 43/00* (2006.01)
*A61K 31/33* (2006.01)

(52) U.S. Cl.
USPC ...... 514/183; 514/214.01; 514/283; 540/576; 546/58; 546/42

(58) Field of Classification Search ............. 514/214.01, 514/283; 540/576; 546/58, 42
See application file for complete search history.

(56) References Cited

U.S. PATENT DOCUMENTS

2006/0014772 A1 * 1/2006 Lee et al. ............ 514/283

OTHER PUBLICATIONS

Haring et al, Current Opinion in Microbiology, 2001, 4:462-466.*
Xu, Weiming, et al. "The role of nitric oxide in cancer" *Cell Research* (2002); 12(5-6):311-320.
Yang, Cheng-Wei, et al. "Novel Small-Molecule Inhibitors of Transmissible Gastroenteritis Virus" *Antimicrobial Agents and Chemotherapy* Nov. 2007, p. 3924-3931.
Barnard, Dale L. "Enhancement of the infectivity of SARS CoV in BALB/c mice by IMP dehydrogenase inhibitors,m including ribavirin" *Antiviral Research* 71 (2006) 53-63.
Olson, SY, et al. "Regulation of apoptosis-related genes by nitric oxide in cancer" *Nitric Oxide* Sep. 2008; 19(2):170-6 (abstract only).

* cited by examiner

*Primary Examiner* — Brandon Fetterolf
*Assistant Examiner* — Jean Cornet
(74) *Attorney, Agent, or Firm* — Occhiuti Rohlicek & Tsao LLP

(57) ABSTRACT

Treatment of coronavirus infection with phenanthroindolizidine analogues.

16 Claims, No Drawings

PHENANTHROINDOLIZIDINE ANALOGUES

CROSS REFERENCE TO RELATED APPLICATIONS

This application claims priority to U.S. Provisional Application Ser. Nos. 61/154,825 and 61/154,826, both filed Feb. 24, 2009. The contents of these two prior applications are hereby incorporated by reference in their entireties.

BACKGROUND

Coronavirus (CoV) is a family of enveloped viruses that have a positive-sense single-stranded RNA genome.

CoV infects the upper respiratory and gastrointestinal tract of mammals and birds, causing various diseases. For example, CoV infection leads to severe acute respiratory syndrome (SARS), a life-threatening disease, and common cold in humans, and gastrointestinal or respiratory diseases in farm animals or domesticated pets.

No effective treatment has been developed currently to cure diseases associated with CoV infection, including SARS.

SUMMARY

The present invention is based on the unexpected discovery that certain phenanthroindolizidine analogues exhibited anti-CoV activity, i.e., reducing CoV-induced cytopathic effects or inhibiting viral protein production and viral replication.

In one aspect, this invention features a method of treating infection by Cov (e.g., SARS-associated virus and transmissible gastroenteritis virus) with a compound of Formula I:

Formula I 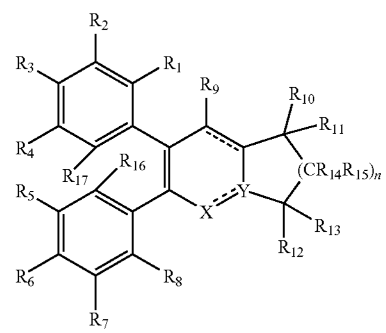 wherein n is 1, 2 or 3; each of ---- and ----, independently, is a single bond or a double bond; each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, carbonyloxy, or amino; each of $R_{16}$ and $R_{17}$, independently, is H, halogen, alkyl, aryl, cyclyl, heteroaryl, heterocyclyl, OH, alkoxy, carbonyloxy, or amino, or $R_{16}$ and $R_{17}$ together are a single bond; and when ---- is a single bond, X is C═O or CR'R" and Y is N or $N^+\rightarrow O^-$, and when ---- is a double bond, X is CR', Y is $N^+$, and a counterion coexists in the compound; each of R' and R", independently, being H, halo, alkyl, aryl, cyclyl, heteroaryl, heterocyclyl, OH, alkoxy, or amino. Note that when $R_{16}$ and $R_{17}$ together are a single bond, the above formula contains a phenanthrene moiety. One skilled in the art would recognize that this "single bond" is conjugated with the other bonds within the phenanthrene moiety to form an aromatic bonding system. See, e.g., J. McMurry, Organic Chemistry, $4^{th}$ Edition, 1996, Brook/Cole, page 543-545.

Referring to Formula I, a subset of the compounds described above have one or more of the following features: each of $R_2$ and $R_3$, independently, is OH or alkoxy; each of $R_1$, $R_5$ and $R_8$ is H; each of $R_6$ and $R_7$, independently, is OH or alkoxy; $R_9$ is OH, alkoxy, or carbonyloxy, and each of $R_{10}$, $R_{11}$, $R_{12}$, $R_{13}$, $R_{14}$, and $R_{15}$ is H.

In another aspect, this invention features the compounds of Formula II:

Formula II 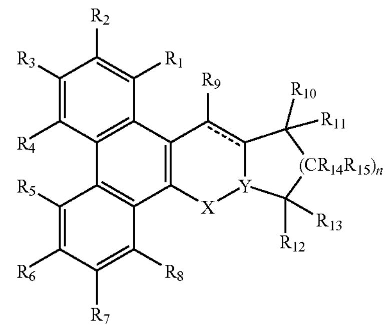 in which ---- is a single bond or a double bond; n is 2 or 3; X is CRR' or C═O in which each of R and R', independently, is H, halo, alkyl, aryl, cyclyl, heteroaryl, heterocyclyl, OH, alkoxy, or amino; Y is N or $N^+\rightarrow O^-$; and when n is 2 and Y is N, each of $R_1$, $R_4$, $R_5$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, carbonyloxy, or amino, and either (i) one of $R_2$, $R_3$, $R_6$ and $R_7$ is OH and each of the others, independently, is OH, alkoxy, alkyl, aryl, cyclyl, heteroaryl, or heterocyclyl, or (ii) each of $R_7$ and $R_9$, independently, is halogen, alkyl, aryl, cyclyl, heteroaryl, heterocyclyl, OH, alkoxy, or amino; or when n is 2 and Y is $N^+\rightarrow O^-$ or when n is 3 and Y is N or $N^+\rightarrow O^-$ each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, carbonyloxy, or amino.

Referring to Formula II, a subset of the compounds described above have one or more of the following features: each of $R_1$, $R_5$ and $R_8$ is H; each of $R_2$ and $R_3$, independently, is OH or alkoxy; each of $R_6$ and $R_7$, independently, is OH or alkoxy; ---- is a single bond; and each of $R_{10}$, $R_{11}$, $R_{12}$, $R_{13}$, $R_{14}$, and $R_{15}$ is H.

In still another aspect, this invention features the compounds of Formula III:

Formula III wherein n is 1, 2, or 3; Y is N or $N^+ \rightarrow O^-$; and when n is 1, X is C═O, each of $R_1$, $R_5$, $R_6$, $R_7$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, or amino, and each of $R_2$, $R_3$, and $R_4$, independently, is alkoxy; or when n is 2 or 3, X is CRR' or C═O, in which each of R and R', independently, is H, halo, alkyl, aryl, cyclyl, heteroaryl, heterocyclyl, OH, alkoxy, or amino, each of $R_1$, $R_2$, $R_3$, $R_4$, $R_5$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, or amino; and each of $R_6$ and $R_7$, independently, is alkoxy.

Referring to Formula III, a subset of the compounds described above have one or more of the following features: n is 1; each of $R_2$, $R_3$, and $R_4$, independently, is alkoxy; each of $R_6$ and $R_7$, independently, is alkoxy; X is C═O; and $R_9$ is H.

Also referring to Formula III, another subset of the compounds described above have one or more of the following features: n is 2 or 3; each of $R_6$ and $R_7$, independently, is alkoxy; $R_1$, $R_2$, and $R_4$ is H and $R_3$, independently, is alkoxy, or $R_1$ is H and each of $R_2$, $R_3$, and $R_4$, independently, is alkoxy; and X is $CH_2$ or C═O.

Further within the scope of this invention is use of one of the above-described compounds for treating CoV infection or for manufacture of a medicament for this therapy.

The term "alkyl" refers to a straight or branched hydrocarbon, containing 1-10 carbon atoms. Examples of alkyl groups include, but are not limited to, methyl, ethyl, n-propyl, i-propyl, n-butyl, i-butyl, and t-butyl. The term "alkoxy" refers to a univalent radical alkyl-O—, e.g. $CH_3O$—. The term "carbonyloxy" refers to a radical moiety of R—C(O)—O—, wherein R is alkyl, cyclyl, heterocyclyl, aryl, or heteroaryl.

The term "aryl" refers to a 6-carbon monocyclic, 10-carbon bicyclic, 14-carbon tricyclic aromatic ring system wherein each ring may have 1 to 4 substituents. Examples of aryl groups include, but are not limited to, phenyl, naphthyl, and anthracenyl.

The term "cyclyl" refers to a saturated and partially unsaturated cyclic hydrocarbon group having 3 to 12 carbons, preferably 3 to 8 carbons, and more preferably 3 to 6 carbons, wherein the cyclyl group may be optionally substituted. Examples of cyclyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein each ring may have 1 to 4 substituents. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

Alkyl, aryl, cyclyl, heteroaryl, and heterocyclyl mentioned herein include both substituted and unsubstituted moieties. Examples of a substituent include, but are not limited to, halo, hydroxyl, amino, cyano, nitro, mercapto, alkoxycarbonyl, amido, carboxy, alkanesulfonyl, alkylcarbonyl, carbamido, carbamyl, carboxyl, thioureido, thiocyanato, sulfonamido, alkyl, alkenyl, alkynyl, alkyloxy, aryl, heteroaryl, cyclyl, heterocyclyl, in which alkyl, alkenyl, alkynyl, alkyloxy, aryl, heteroaryl cyclyl, and heterocyclyl are optionally further substituted with alkyl, aryl, heteroaryl, halogen, hydroxyl, amino, mercapto, cyano, or nitro.

The term "anion" refers to a negatively charged ion. Examples of an anion include, but are not limited to, $Cl^-$, $Br^-$, $I^-$, $SO_4^{2-}$, $PO_4^{3-}$, $ClO_4^-$, $CH_3CO_2^-$, and $CF_3CO_2^-$.

Shown in Table 1 below are exemplary compounds of Formulas I, II, and III:

TABLE 1

| Compound No. | Structure |
| --- | --- |
| 1 | 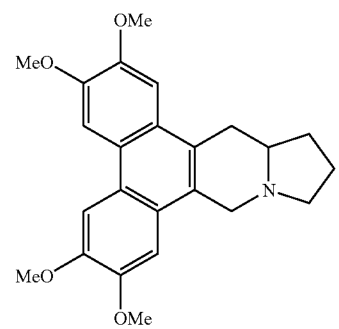 [SMILES: COc1cc2c3c(c4cc(OC)c(OC)cc4c2cc1OC)CN1CCCC1C3]  |
| 2 | 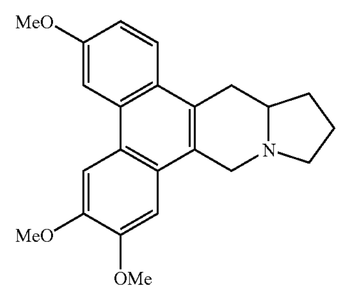 [SMILES: COc1ccc2c3c(c4cc(OC)c(OC)cc4c2c1)CN1CCCC1C3]  |
| 3 | 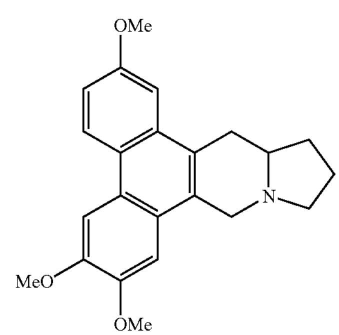 [SMILES: COc1ccc2c(c1)c1c(c3cc(OC)c(OC)cc32)CN2CCCC2C1]  |

TABLE 1-continued

| Compound No. | Structure |
|---|---|
| 4 | (structure: phenanthroindolizidine with OMe at two positions on top ring, OMe and OMe on bottom ring) |
| 5 | (structure: phenanthroindolizidine with OMe, OMe on top ring and OMe on bottom ring) |
| 6 | (structure: phenanthroindolizidine with OH substituent; OMe groups at indicated positions) |
| 7 | (structure: phenanthroindolizidinone with four OMe groups and C=O) |
| 8 | (structure: phenanthroindolizidine N-oxide with four OMe groups) |
| 9 | (structure: phenanthroindolizinium bromide with four OMe groups, Br⁻) |
| 10 | (structure: phenanthroindolizinium bromide isomer with four OMe groups, Br⁻) |
| 11 | (structure: phenanthroquinolizidine with four OMe groups) |
| 12 | (structure: phenanthroquinolizidine with OH substituent and four OMe groups) |

TABLE 1-continued

| Compound No. | Structure |
|---|---|
| 13 | (structure) |
| 14 | (structure) |
| 15 | (structure) |
| 16 | (structure) |
| 17 | (structure) |
| 18 | (structure) |
| 19 | (structure) |
| 20 | (structure) |
| 21 | (structure) |

TABLE 1-continued

| Compound No. | Structure |
|---|---|
| 22 | (structure) |
| 23 | (structure) |
| 24 | (structure) |
| 25 | (structure) |
| 26 | (structure) |
| 27 | (structure) |
| 28 | (structure) |
| 29 | (structure) |
| 30 | (structure) |

TABLE 1-continued
| Compound No. | Structure |
|---|---|
| 31 | 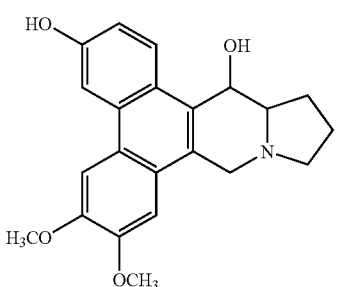 |
| 32 | 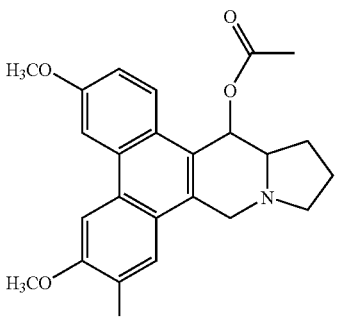 |
| 33 | 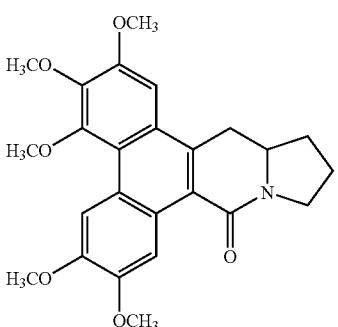 |
| 34 | 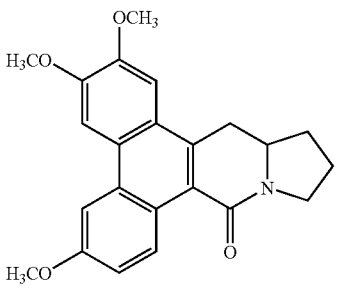 [SMILES: COc1ccc2c3c(c4cc(OC)c(OC)cc4c2c1)CC1CCCN1C3=O] |
| 35 | 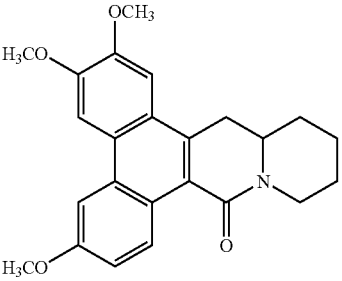 [SMILES: COc1ccc2c3c(c4cc(OC)c(OC)cc4c2c1)CC1CCCCN1C3=O] |
| 36 | 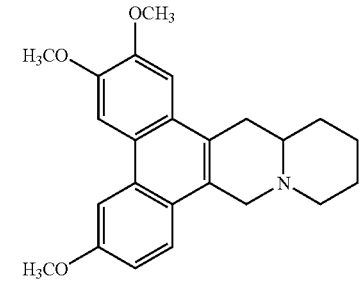 [SMILES: COc1ccc2c3c(c4cc(OC)c(OC)cc4c2c1)CC1CCCCN1C3] |
| 37 | 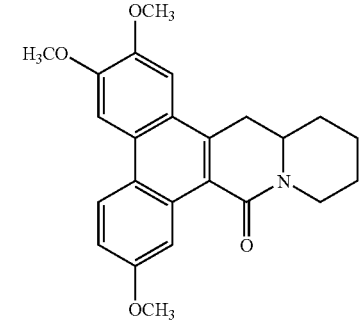 [SMILES: COc1ccc2c(c1)c1c(c3cc(OC)c(OC)cc32)CC2CCCCN2C1=O] |
| 38 | 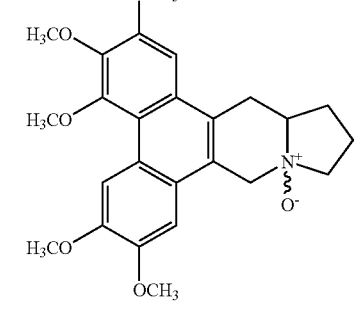 |
| 39 | 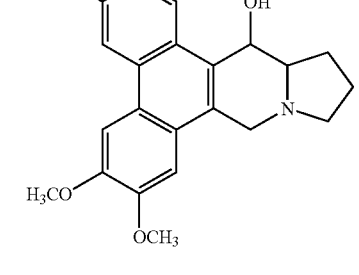 |
| 40 | 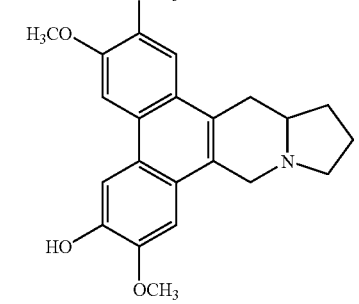 |

TABLE 1-continued

| Compound No. | Structure |
|---|---|
| 41 | 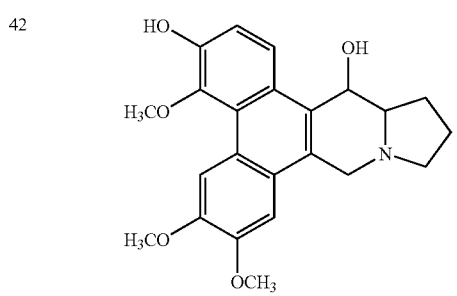 |
| 42 | 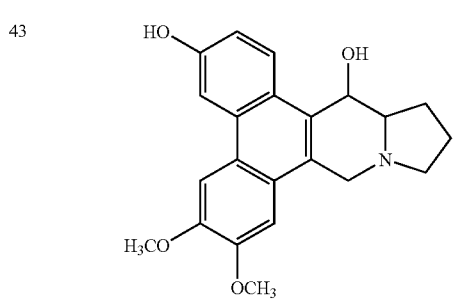 |
| 43 | 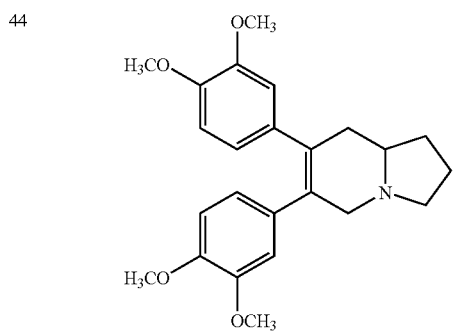 |
| 44 | 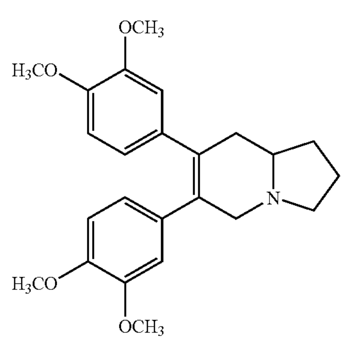 [SMILES: COc1ccc(C2=C(c3ccc(OC)c(OC)c3)CN3CCCC3C2)cc1OC] |

TABLE 1-continued

| Compound No. | Structure |
|---|---|
| 45 | 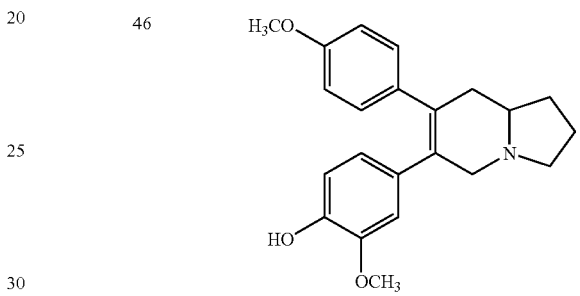 |
| 46 | 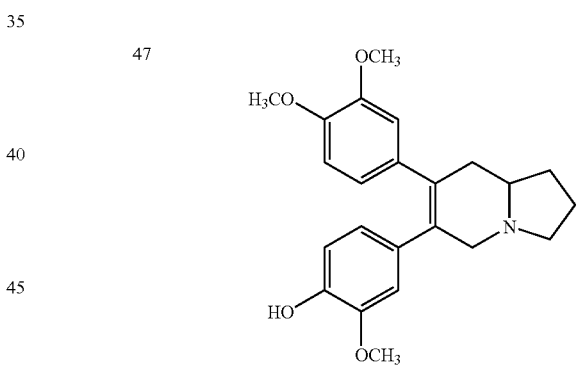 |
| 47 | |

The details of many embodiments of the invention are set forth in the description below. Other features, objects, and advantages of the invention will be apparent from the description and the claims.

DETAILED DESCRIPTION

Some of the compounds described above can be isolated from natural sources. For example, Compounds 1-6 and 29-31 can be obtained from *Tylophora indica* or *Tylophora ovata* using modified known extraction and purification methods. See, e.g., Yang et al., Biochemical and Biophysical Research Communication, 2007, 354(4): 942-8. Some compounds can also be synthesized by conventional methods. For example, one can prepare Compounds 1 and 11 via the synthetic route depicted in Scheme 1 below.

Scheme 1

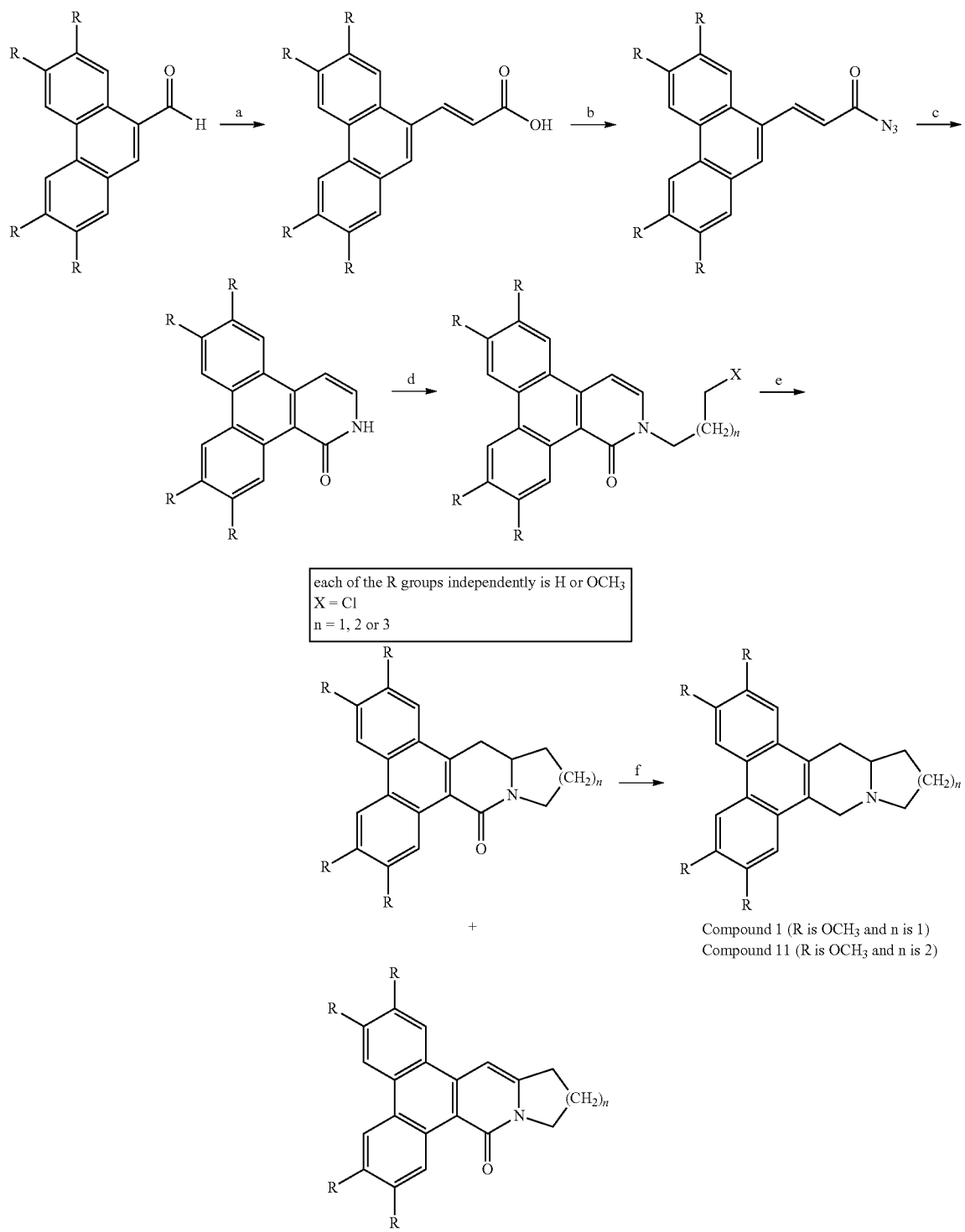

Reagents and condition: (a) (i) Ph₃P=CHCO₂Et, toluene, reflux, 4 h; (ii) KOH, EtOH—H₂O, reflux, 3 h; (b) (i) (COCl)₂, toluene, 80° C., 5 h; (ii) NaN₃, acetone, rt, 2 h; (c) cat. Hg(OAc)₂, o-dichlorobenzene, reflux, 1 h; (d) (i) NaH, DMF; (ii) Br(CH₂)ₙCl, DMF, rt, overnight; (e) 2,2′-azobis(isobutyronitrile) (AIBN), Bu₃SnH, toluene, reflux, 6 h; (f) NaAl(OCH₂CH₂OMe)₂H₂, dioxane, reflux, 2 h.

Scheme 2 below shows that some of the products or intermediates shown in Scheme 1 can be used to prepare other compounds of Formulas I, II, and III via simple transformation. For example, oxidizing Compounds 1 and 11 with H₂O₂ affords N-oxide Compounds 8 and 18, respectively. As another example, treating Compounds 1 and 11 with N-bromosuccunide (NBS) affords Compounds 9 and 19, respectively.

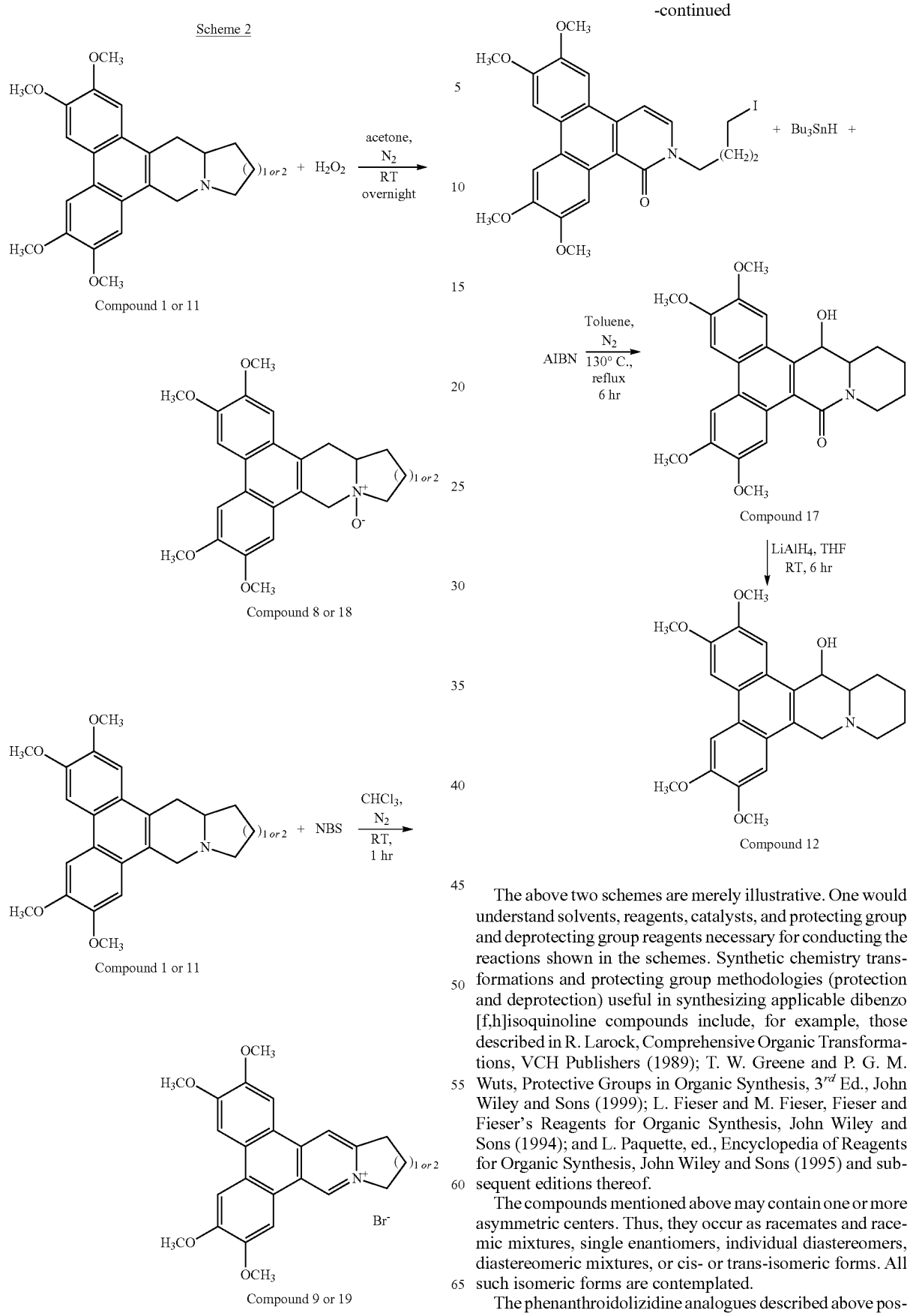

The above two schemes are merely illustrative. One would understand solvents, reagents, catalysts, and protecting group and deprotecting group reagents necessary for conducting the reactions shown in the schemes. Synthetic chemistry transformations and protecting group methodologies (protection and deprotection) useful in synthesizing applicable dibenzo[f,h]isoquinoline compounds include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995) and subsequent editions thereof.

The compounds mentioned above may contain one or more asymmetric centers. Thus, they occur as racemates and racemic mixtures, single enantiomers, individual diastereomers, diastereomeric mixtures, or cis- or trans-isomeric forms. All such isomeric forms are contemplated.

The phenanthroidolizidine analogues described above possess anti-CoV activity. Thus, one can use an effective amount of a phenanthroidolizidine compound (i.e., a compound of Formula I) to treat CoV infection. The term "treating" refers to administering the compound to a subject who has CoV infection, a symptom of the infection, or a predisposition toward the infection, with the purpose to cure, heal, alleviate, relieve, alter, remedy, ameliorate, improve, or affect the infection, the symptoms of the infection, or the predisposition toward the infection. The term "an effective amount" refers to the amount of the compound that is required to confer one of the above-described effects on the subject, either alone or in combination with one or more additional active agents. The effective amount varies, as recognized by those skilled in the art, depending on the types of the effects, route of administration, excipient usage, and the possibility of co-usage with other treatment.

When used for treating CoV infection, the compounds described herein can be in isolated form, i.e., prepared by a synthetic method or enriched from a natural source. An isolated phenanthroindolizidine compound refers to a preparation that contains at least 40% of the compound by dry weight. Purity of an isolated compound can be measured by, e.g., column chromatography, mass spectrometry, high performance liquid chromatography (HPLC), NMR, or any other suitable methods.

The CoV infection to be treated by the method of this invention can be caused by human CoV 229E, transmissible gastroenteritis virus (TGEV), mouse hepatitis virus, bovine CoV, infectious bronchitis virus, Feline coronaviruses (FCoV), or a SARS-associated CoV (SARS CoV).

To practice the methods of the present invention, a composition having one or more of the above-described phenanthroindolizidine compounds can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol and water. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art. A composition having one or more active phenanthroindolizidine compounds can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active phenanthroindolizidine compound. Examples of other carriers include colloidal silicon oxide, magnesium stearate, cellulose, sodium lauryl sulfate, and D&C Yellow #10.

The above-described anti-viral effect of a phenanthroindolizidine compound can be tested by an in vitro or in vivo assay. For example, compounds of Formula I can be preliminarily screened by in vitro assays in which the compounds are tested for their efficacy in inhibiting CoV-induced cytopathic effects. Compounds that show high efficacy in the preliminary screening can be further evaluated by in vivo methods well known in the art to evaluate their activity in treating CoV infection.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Chemical Synthesis

Compounds 1, 7, 11, 13-16, and 20 were synthesized by the methods illustrated in the following scheme:

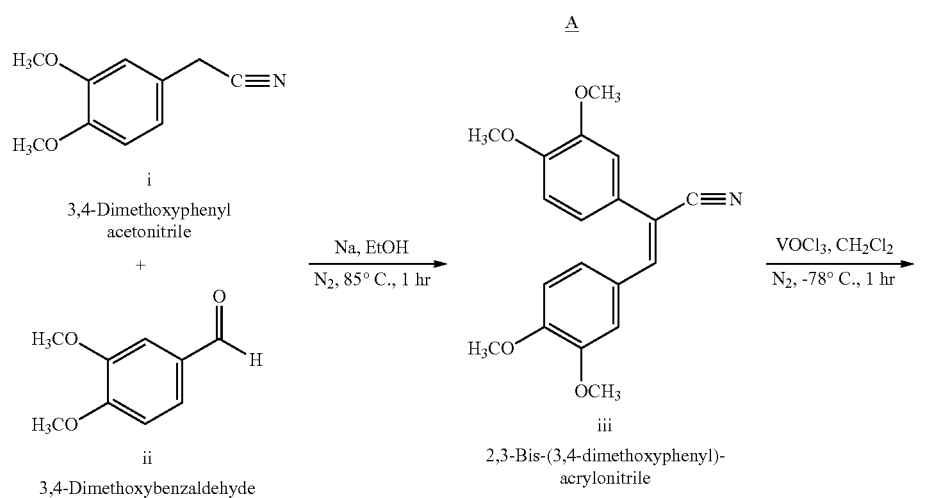
A
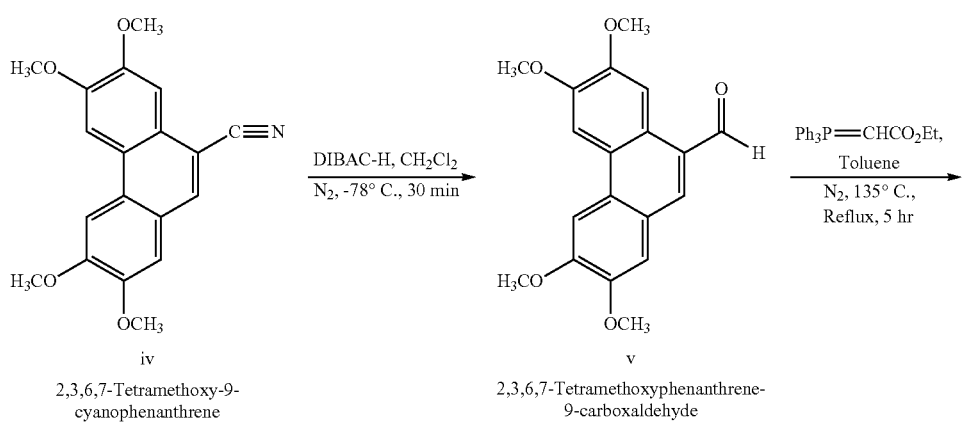
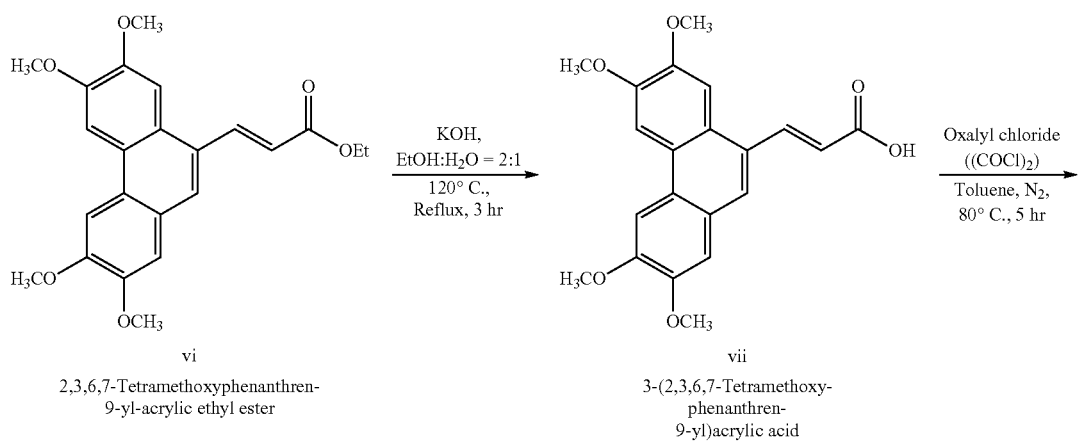

-continued
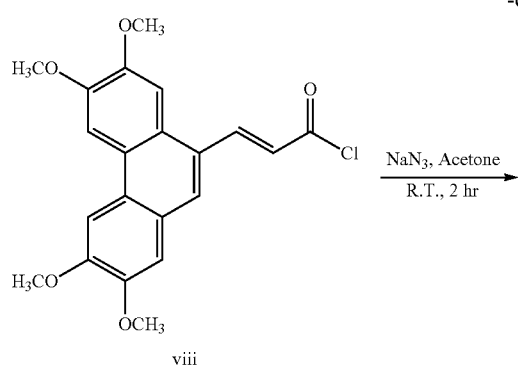
viii
3-(2,3,6,7-Tetramethoxy-
phenanthren-
9-yl)acryloyl chloride
NaN₃, Acetone
R.T., 2 hr
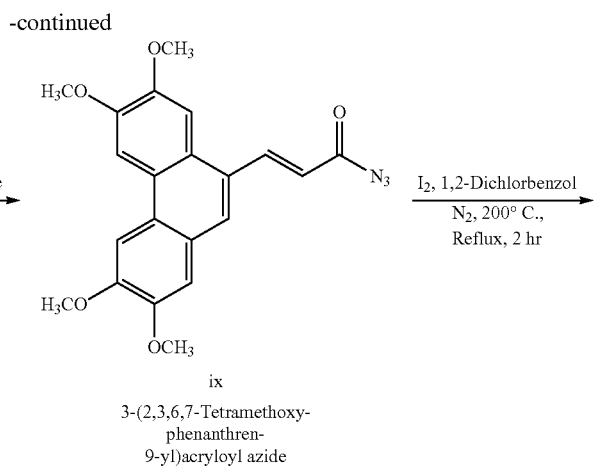
ix
3-(2,3,6,7-Tetramethoxy-
phenanthren-
9-yl)acryloyl azide
I₂, 1,2-Dichlorbenzol
N₂, 200° C.,
Reflux, 2 hr
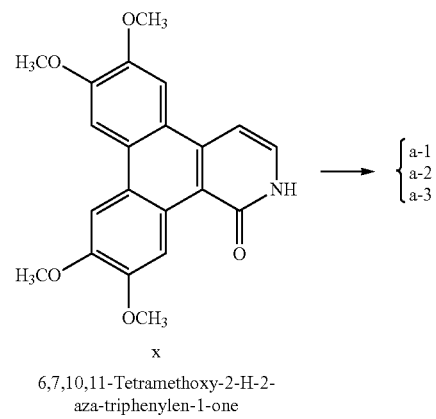
x
6,7,10,11-Tetramethoxy-2-H-2-
aza-triphenylen-1-one
→ { a-1, a-2, a-3 }
a-1.
1-Brom-3-
chlorpropan
NaH, DMF,
N₂, R.T.,
Over Night
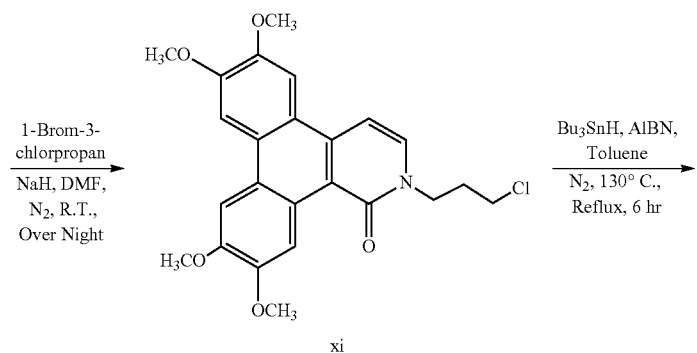
xi
Bu₃SnH, AlBN,
Toluene
N₂, 130° C.,
Reflux, 6 hr
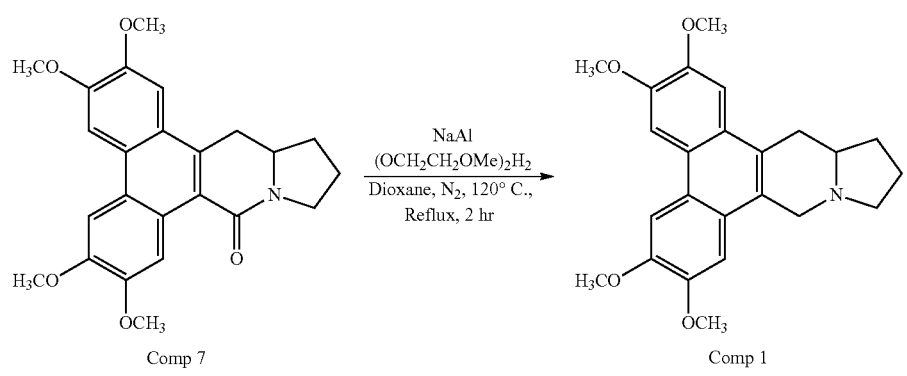
Comp 7
NaAl
(OCH₂CH₂OMe)₂H₂
Dioxane, N₂, 120° C.,
Reflux, 2 hr
Comp 1
a-2.

-continued
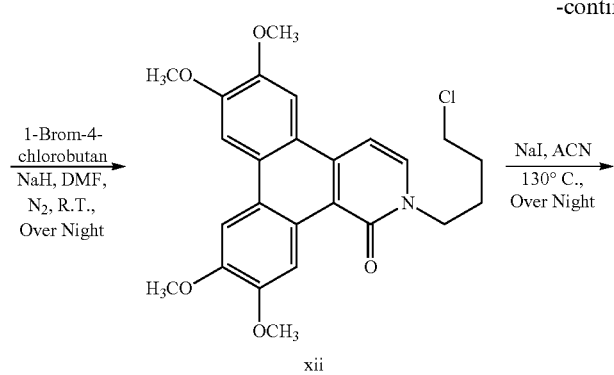
xii
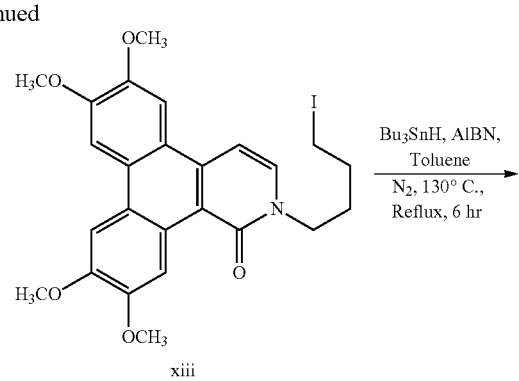
xiii
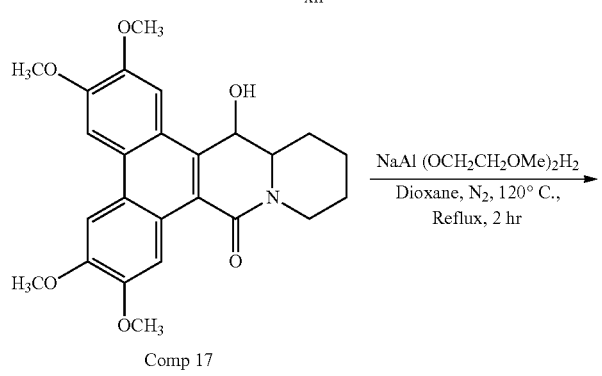
Comp 17
+
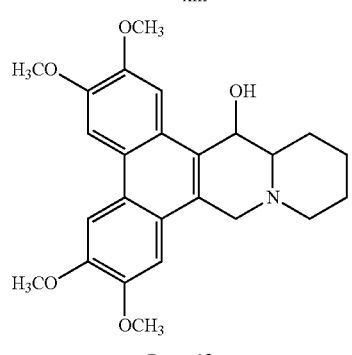
Comp 12
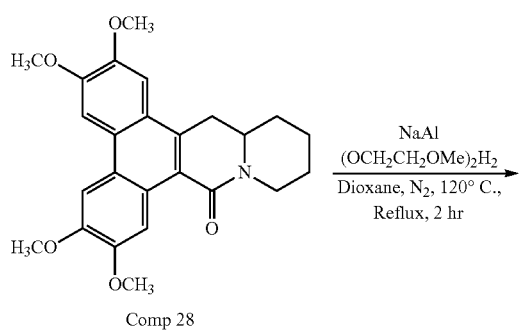
Comp 28
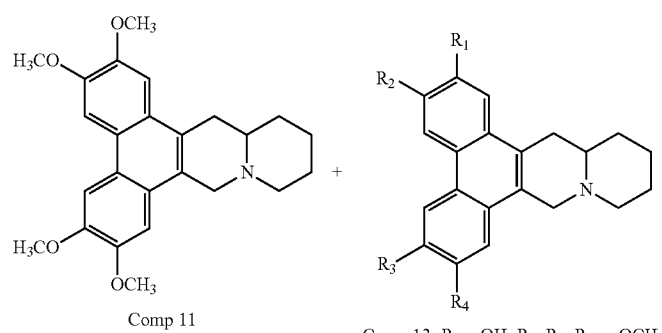
Comp 11
Comp 13: R₁ = OH, R₂, R₃, R₄, = OCH₃
Comp 14: R₂ = OH, R₁, R₃, R₄, = OCH₃
Comp 15: R₃ = OH, R₁, R₂, R₄, = OCH₃
Comp 16: R₄ = OH, R₁, R₂, R₃, = OCH₃
(Mix)
a-3.
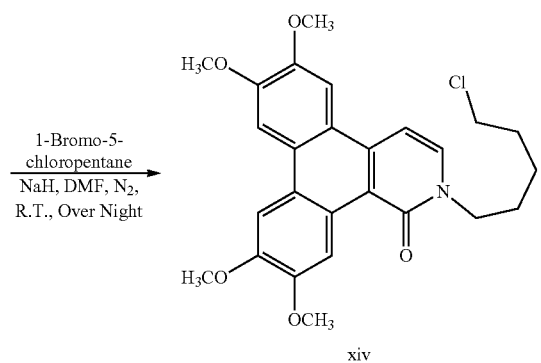
xiv
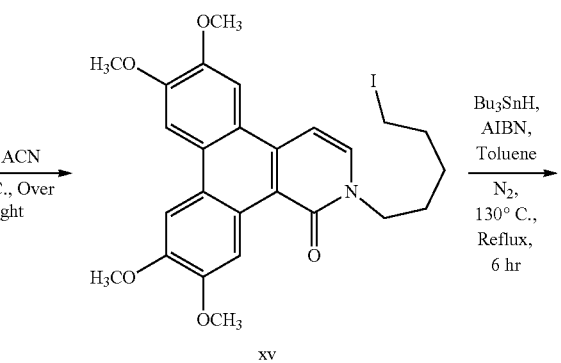
xv

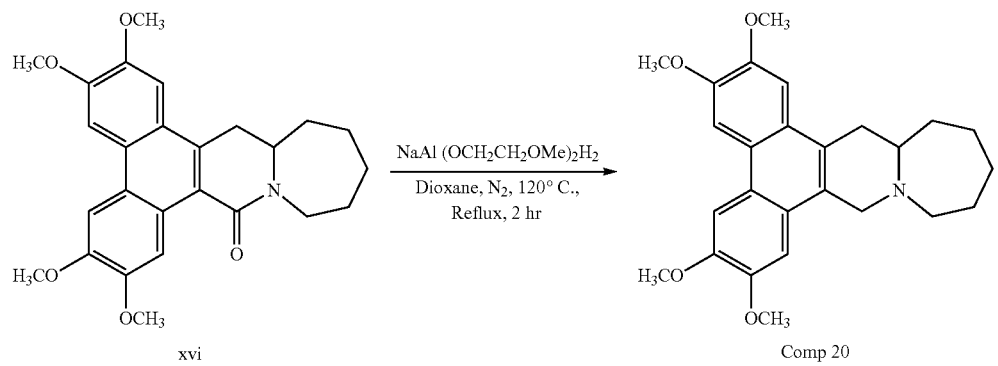

VOCl₃: Vanadium oxytrichloride
DIBAC-H: Diisobutylaluminumhydride
(COCl)₂: Oxalyl chloride
Ph₃P=CHCO₂Et: Ethyl (Triphenylphosphoranylidene) acetate
Bu₃SnH: Tri-n-Butyltin hydride
AIBN: 2, 2′-Azobisisobutyronitrile)
NaAl (OCH₂CH₂OMe)₂H₂: Sodium bis (2-methoxyethoxy) aluminum hydride Compounds i and ii were condensed to afford acrylonitrile compound iii, which was cyclized to give 9-cyanophenanthrene compound iv. The cyano group of compound 1v was reduced to aldehyde to provide compound v, which was subjected to Wittig reaction, hydrolysis, and acyl chlorination to produce acyl chloride viii. Compound viii was reacted with sodium azide to give acyl azide xi, which underwent arrangement to provide compound x.

Compound x was coupled with 1-bromo-4-chloropropane to afford compound xi. Cyclization of compound xi provided compound 7, which was reduced to compound 1.

Compound x was coupled with 1-bromo-4-chlorobutane to afford compound xii, which was reacted with sodium iodide to give iodo compound xiii. Cyclization of iodo compound xiii provided a mixture of compound 17 and compound 28. Reduction of compound 17 gave compound 11. Partial hydrolysis of Compound 28 gave a mixture of compounds 13-16.

Compound x was coupled with 1-bromo-5-chloropentane to give compound xiv, which was reacted with sodium iodide to give iodo compound xv. Cyclization of iodo compound xv gave compound xvi, which was reduced to afford compound 20.

Compounds 2 and 21-27 were synthesized by the methods illustrated in the following scheme:

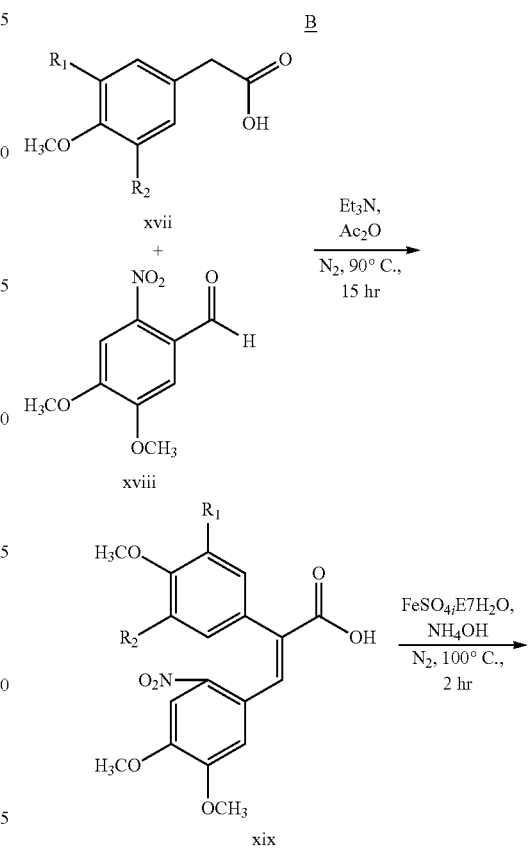

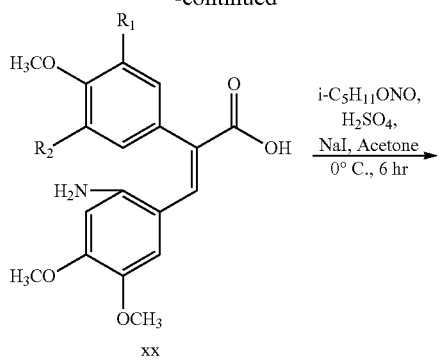
xx
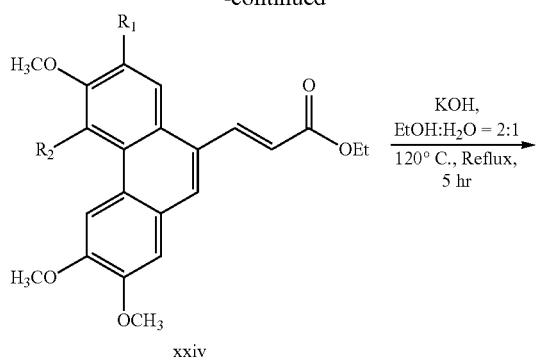
xxiv
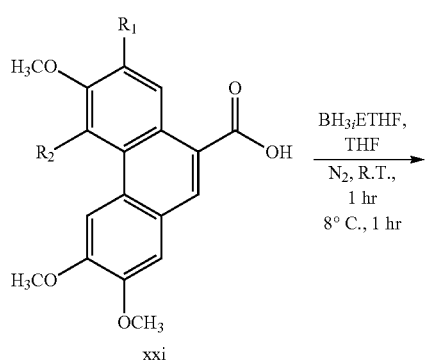
xxi
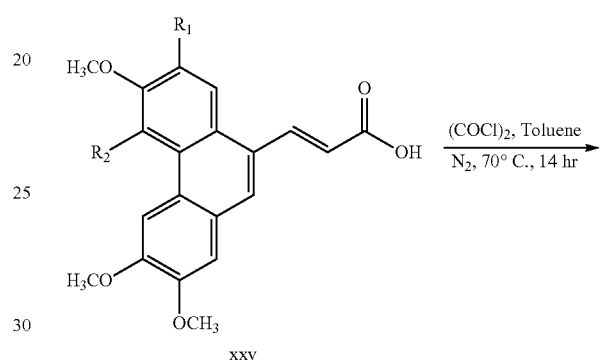
xxv
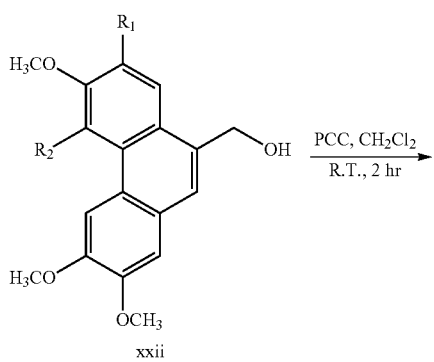
xxii
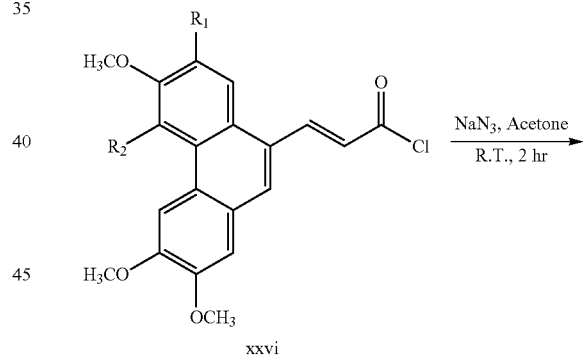
xxvi
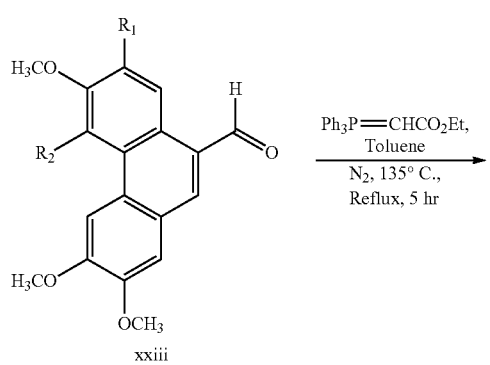
xxiii
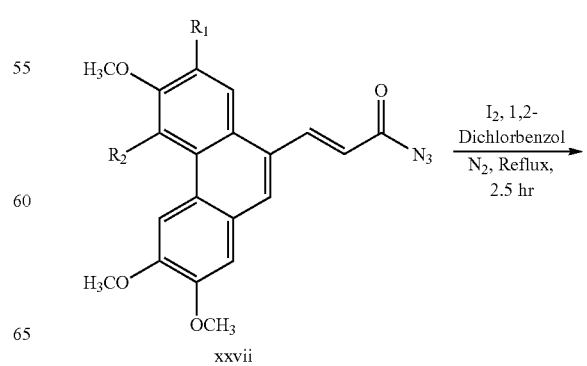
xxvii

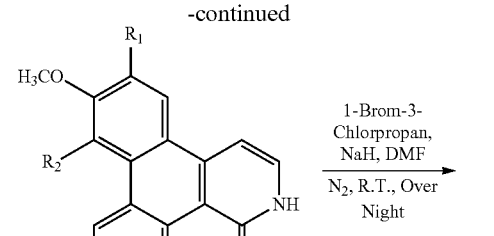

xxviii

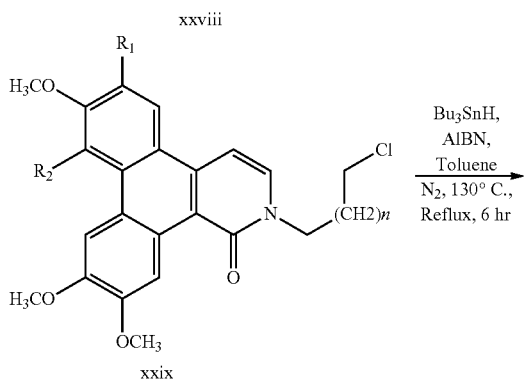

xxix

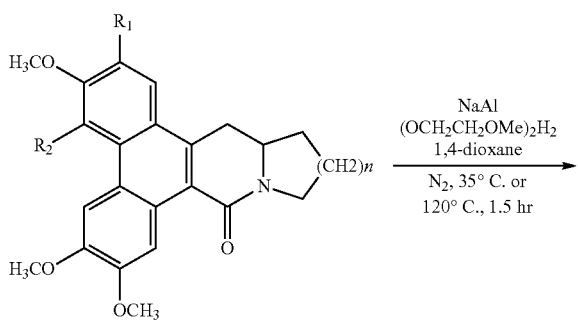

Comp 21: $R_1, R_2 = H, n = 1$
Comp 23: $R_1, R_2 = OCH_3, n = 1$
Comp 25: $R_1, R_2 = H, n = 2$
Comp 27: $R_1, R_2 = OCH_3, n = 2$

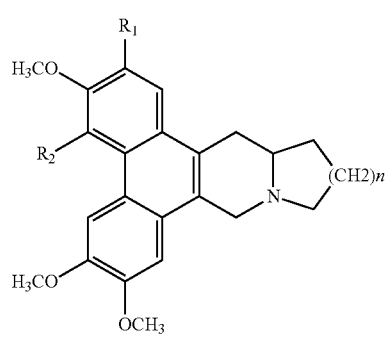

Comp 2: $R_1, R_2 = H, n = 1$
Comp 22: $R_1, R_2 = OCH_3, n = 1$
Comp 24: $R_1, R_2 = H, n = 2$
Comp 26: $R_1, R_2 = OCH_3, n = 2$ i-C$_5$H$_{11}$ONO: Isoamyl nitrite
PCC: Pyridinium chlorochromate
(COCl)$_2$: Oxalyl chloride
Ph$_3$P═CHCO$_2$Et: Ethyl (Triphenylphosphoranylidene) acetate
Bu$_3$SnH: Tri-n-Butyltin hydride
AIBN: 2,2'-Azobisisobutyronitrile)
NaAl(OCH$_2$CH$_2$OMe)$_2$H$_2$: Sodium bis (2-methoxyethoxy) aluminum hydride Compounds xvii and xviii were condensed to afford acrylocraboxylic acid compound xix, which underwent cyclization to give 9-cyanophenanthrene compound xxi. Reduction of the carboxylix acid to aldehyde afforded compound xxiii, which underwent Wittig reaction, hydrolysis, and acyl chlorination to afford acyl chloride xxvi. Compound xxvi was reacted with sodium azide to give acyl azide xxvii, which underwent arrangement to provide compound xxviii. Compound xxviii was coupled with 1-bromo-3-chloropropane or 1-bromo-4-chlorobutane and subsequently cyclized to afford compound 21, 23, 25, and 27, which were reduced to compounds 2, 22, 24, and 26, respectively.

Further, compounds 1, 6, 9-11, 19, 25, 31, 32, 34, 39-42, and 44-47 were prepared as follows:

Compounds 1, 6, 35, and 43 were obtained from extracting *Tylophora indica* and *Tylophora ovata* with methanol, followed by purification using chromatography, such as silica-gel column chromatography and high-pressure liquid chromatography.

Compound 1, IR (KBr) cm$^{-1}$: 1616, 1512, and 1468 (aromatic C═C); CI MS m/z 394 (M+H)$^+$; $^1$H-NMR (400 MHz, CDCl$_3$): 1.78 (1H, m), 1.93 (1H, m), 2.04 (1H, m), 2.24 (1H, m), 2.47 (1H, d, J=9.0 Hz), 2.50 (1H, m), 2.92 (1H, dd, J=15.6 Hz, J=10.8 Hz), 3.38 (1H, dd, J=15.6 Hz, J=2.4 Hz), 3.47 (1H, t, J=9.0 Hz), 3.67 (1H, d, J=14.6 Hz), 4.05 (6H, s), 4.12 (6H, s), 4.63 (1H, d, J=14.6 Hz), 7.16 (1H, s), 7.32 (1H, s), 7.82 (1H, s), 7.83 (1H, s).

Compound 6, white crystals; mp 228-229° C.; IR (KBr) cm$^{-1}$: 3182 (OH), 1617, 1512, and 1469 (aromatic C═C); $^1$H NMR (600 MHz, CDCl$_3$): 1.91 (2H, m), 2.02 (1H, m), 2.26 (1H, m), 2.40 (2H, m), 3.12 (1H, t, J=14.2 Hz), 3.32 (1H, t, J=7.8 Hz), 3.55 (1H, m), 3.85 (3H, s), 4.05 (3H, s), 4.10 (3H, s), 4.96 (1H, br), 6.32 (1H, d, J=22.8 Hz), 7.26 (1H, dd, J=9 Hz, J=2.4 Hz), 7.62 (1H, d, J=10.2 Hz), 7.76 (1H, d, J=2.4 Hz), 8.41 (1H, dd, J=9 Hz, J=4.2 Hz); $^{13}$C-NMR (150 MHz, CDCl$_3$): 21.9, 23.9, 53.4, 55.4, 55.5, 55.7, 64.5, 65.3, 102.8, 103.0, 104.2, 114.8, 123.7, 124.2, 125.3, 128.9, 130.6, 148.5, 148.7, 157.5.

Compound 35, brown solid; mp 136~138° C.; (c=0.055, CHCl$_3$: MeOH=1:1); IR (KBr) cm$^{-1}$: 3406 (OH), 3172 (OH), 1604, 1514, and 1467 (aromatic C═C); EI-MS m/z (rel. int.): 395 [M]$^+$ (19), 326 (100); HR-EI-MS m/z: 395.1732 (calcd for C$_{23}$H$_{25}$NO$_5$, 395.1726); $^1$H NMR (600 MHz, CDCl$_3$): 1.96 (3H, m), 2.36 (2H, m), 2.47 (1H, m), 3.30 (1H, d, J=15 Hz), 3.31 (1H, m), 3.82 (3H, s), 3.90 (3H, s), 3.94 (1H, d, J=15 Hz), 4.09 (3H, s), 4.99 (1H, s), 6.61 (1H, s), 7.34 (1H, d, J=9 Hz), 8.23 (1H, d, J=9.6 Hz), 8.87 (1H, s); $^{13}$C NMR (150 MHz, CDCl$_3$): 22.1, 24.1, 53.8, 55.4, 55.5, 55.6, 60.3, 64.8, 65.1, 102.5, 107.8, 115.5, 122.1, 122.8, 122.9, 125.2, 126.5, 129.8, 142.6, 147.2, 148.3, 148.5.

Compound 43, brown solid; mp 189~190° C.; IR (KBr) cm$^{-1}$: 3350 (OH), 1604, 1516, and 1456 (aromatic C═C); EI-MS m/z (rel. int.): 365 [M]$^+$ (14), 296 (100); HR-EI-MS m/z: 365.1620 (calcd for C$_{22}$H$_{23}$NO$_4$, 365.1621); $^1$H NMR (600 MHz, DMSO-d$_6$): 1.83 (3H, m), 2.18 (1H, m), 2.38 (2H, m), 3.33 (1H, m), 3.41 (1H, m), 3.92 (3H, s), 3.99 (3H, s), 4.51 (1H, m), 4.58 (1H, m), 4.91 (1H, d, J=8.4 Hz), 7.10 (1H, dd, J=2.1 Hz, J=8.7 Hz), 7.17 (1H, s), 7.91 (1H, s), 7.93 (1H, d, J=2.1 Hz), 8.14 (1H, d, J=8.7 Hz); $^{13}$C NMR (150 MHz, DMSO-d$_6$): 21.6, 23.9, 53.5, 54.9, 55.5, 63.6, 64.9, 103.8, 103.9, 106.0, 116.2, 123.3, 123.9, 124.2, 125.3, 126.4, 129.7, 130.6, 148.5, 149.1, 155.3.

Compounds 1, 9, 11, 19, 25, and 34 were prepared according to the methods described in Chuang et al., Org Biomol Chem, 2006, 4:860-7; Yang et al., Mol. Pharmacol., 2006, 69:749-58, and Yang et al., Antimicrob Agents Chemother, 2007, 51:3924-31.

Compound 32 was prepared by reacting compound 6 with acetic anhydride and pyridine overnight at room temperature.

Compound 32, white crystals; mp: 196-198° C.; IR (KBr) cm$^{-1}$: 1728 (C=O), 1617, 1515, and 1471 (aromatic C=C); $^1$H NMR (400 MHz, CDCl$_3$): 1.67 (1H, m), 2.02 (2H, m), 2.06 (1H, m), 2.15 (3H, S), 2.46 (1H, d, J=8.8 Hz), 2.72 (1H, t), 3.53 (1H, t), 3.64 (1H, d, J=15.4 Hz), 4.01 (3H, S), 4.06 (3H, S), 4.12 (3H, S), 4.78 (1H, d, J=15.4 Hz), 6.71 (1H, d, J=2.4 Hz), 7.22 (1H, dd, J=8.8 Hz, J=2.4 Hz), 7.87 (1H, d, J=9.2 Hz), 7.91 (1H, d, J=2.8 Hz), 7.92 (1H, S); CI MS m/z 362 (M-CH$_3$COOH+H)$^+$.

Compound 1, 29, 31, 39, 40-42, and 44-47 were extracted from leaves and stems of *T. ovata*. The air-dried leaves (1.4 kg) and stems (0.6 kg) of *Tylophora ovata* were refluxed with methanol. Evaporation of the solvent under reduced pressure yielded 356 g (leaves) and 127 g (stems) of a green-brown gummy residue. This residue was dissolved in 0.5% HCl and filtered. The filtrate was treated with 25% NH$_4$OH (pH=9), and extracted repeatedly with CHCl$_3$ until the organic layer became negative in the Dragendorff test. The combined CHCl$_3$ portions were evaporated to afford a residue (14.8 g) from leaves and a residue (5.5 g) from stems. After purification by silica gel column chromatography eluted with gradient CHCl$_3$:MeOH and repeated preparative HPLC, eight phenanthroindolizidine alkaloids were obtained from the leaves of *Tylophora ovata*, i.e., compound 1 (16.4 mg), compound 29 (127.4 mg), compound 39 (20.9 mg), compound 40 (8 mg), compound 44 (115.5 mg), compound 45 (34.2 mg), compound 46 (12 mg), and compound 47 (12 mg), and seven were obtained from the stems: compound 1 (18.6 mg), compound 29 (28.6 mg), compound 31 (8.6 mg), compound 39 (3 mg), compound 40 (6.7 mg), compound 41 (1.3 mg), and compound 42 (5.2 mg).

Compound 31, brown solid; mp 189~190° C.; UV (MeOH) $\lambda_{max}$ (log ε): 256 (4.54), 285 (4.40), 310 (sh, 4.00), 360 (3.50), with KOH$\lambda_{max}$ (log ε): 320 (3.96), 410 (3.60), IR (KBr) cm$^{-1}$: 3350 (OH), 1604, 1516, and 1456 (aromatic C=C); EI-MS m/z (rel. int.): 365 [M]$^+$ (14), 296 (100); HR-EI-MS m/z: 365.1620 (calcd for C$_{22}$H$_{23}$NO$_4$, 365.1621).

Compound 39, white solid; mp 229~231° C.; UV (MeOH) $\lambda_{max}$ (log ε): 256 (4.36), 284 (4.10), 310 (sh, 3.63); IR (KBr) cm$^{-1}$: 3176 (OH), 1616, 1512, and 1468 (aromatic C=C); EI-MS m/z (rel. int.): 379 [M]$^+$ (10), 310 (100); HR-EI-MS m/z: 379.1789 (calcd for C$_{23}$H$_{25}$NO$_4$, 379.1777).

Compound 40, brown solid; mp 226~227° C.; UV (MeOH) $\lambda_{max}$ (log ε): 255 (4.59), 288 (4.28), 300 (sh, 4.04), 338 (3.10), 355 (2.91), with KOH$\lambda_{max}$ (log ε): 29 (sh, 3.58), 345 (3.44), 360 (sh, 3.16); IR (KBr) cm$^{-1}$: 435 (OH), 1619, 1514 and 1467 (aromatic C=C); EI-MS m/z (rel. int.): 379 [M]$^+$ (45), 310 (100): HR-EI-MS m/z: 379.1778 (calcd for C$_{23}$H$_{25}$NO$_4$, 379.1777).

Compound 41, brown solid; MS m/z (rel. int.): 379 [M]$^+$ (36), 310 (100); HR-EI-MS m/z: 379.1790 (calcd for C$_{23}$H$_{25}$NO$_4$, 379.1777).

Compound 42, brown solid; mp 136~138° C.; UV (MeOH) $\lambda_{max}$ (log ε): 258 (4.56), 282 (sh, 4.25), 315 (sh, 3.83), with KOH$\lambda_{max}$ (log ε): 292 (sh, 4.11), 330 (3.83); IR (KBr) cm$^{-1}$: 3406 (OH), 3172 (OH), 1604, 1514, and 1467 (aromatic C=C): EI-MS m/z (rel. int.): 395 [M]$^+$ (19), 326 (100); HR-EI-MS m/z: 395.1732 (calcd for C$_{23}$H$_{25}$NO$_5$, 395.1726).

Compound 44, white crystal; mp 131~132° C.; UV (MeOH) $\lambda_{max}$ (log ε): 235 (sh, 4.49), 281 (4.34); IR (KBr) cm$^{-1}$: 1602, 1581, 1512, and 1463 (aromatic C=C); EI-MS m/z (rel. int.): 395 [M]$^+$ (16), 326 (28), 138 (100); HR-EI-MS m/z: 395.2088 (calcd for C$_{24}$H$_{29}$NO$_4$, 395.2089).

Compound 45, tawny oil; UV (MeOH) $\lambda_{max}$ (log ε): 259 (4.41), 280 (sh, 4.38); IR (KBr) cm$^{-1}$: 1605, 1513, and 1464 (aromatic C=C); EI-MS m/z (rel. int.): 365 [M]$^+$ (26), 296 (64), 265 (100); HR-EI-MS m/z: 365.1997 (calcd for C$_{23}$H$_{27}$NO$_3$, 365.1984).

Example 2

Inhibition of SARS CoV-Induced Cytopathic Effects

The anti-SARS CoV activity of test compounds 1, 12, and 18 was examined as follows.

Vero E6 cells were cultured in a 96-well tissue culture plate in a minimal essential medium supplemented with 10% heat-inactivated fetal bovine serum (FBS) until the cells formed a near-confluent monolayer in each well. The cells were then treated in a manner shown below and cultured in the medium mentioned above supplemented with 2% FBS:

Negative control: untreated Vero E6 cells (6 wells)

Virus control: Vero E6 cells treated with SARS CoV alone (6 wells)

Positive control: Vero E6 cells treated with both SARS CoV and Alferon®(Hemispherx Biopharma, Inc.), a human leukocyte-derived alfa-n3 interferon (IFN) (6 wells)

Test wells: Vero E6 cells treated with both SARS CoV and one of the test compounds at various concentrations (each compound at a particular concentration was tested in triplicate for its anti-viral activity and in duplicate for its cytotocixity)

The multiplicity of infection (MOI) used in this assay ranged from 0.01 to 0.025. Within this MOI range, the cytopathic effects (CPEs) reached 100% in Vero E6 cells 3-4 days after being infected with SARS CoV.

The negative control (untreated) Vero E6 cells and the treated cells were cultured at 37° C. for 3-4 days, when the virus control cells showed 100% CPEs as observed using a light microscope.

The morphological changes resulting from the cytotoxicity of a test compound or the CPE caused by SARS CoV were graded on a scale of 0-5 based on the morphology of the treated cells as observed under a light microscope. 0 refers to the normal morphology of Vero E6 cells and 5 refers to 100% cytotoxicity or CPE. The values obtained were then normalized against those obtained from the negative control cells.

The results obtained from this study, shown in Table 2 below, indicated that all of Compounds 1, 11, and 19 showed low cytotoxicity per se and effectively reduced the levels of CPEs caused by SARS CoV infection.

TABLE 2

| Anti-SARS CoV Activity | | | |
|---|---|---|---|
| Compound | Anti-SARS CoV IC$_{50}$ (nm) | Vero E6 Cell Cytotoxicity CC$_{50}$ (nM) | Selective Index CC$_{50}$/IC$_{50}$ |
| Compound 1 | 18 | 420 | 23.3 |
| Compound 12 | 14 | >100 | >7.1 |
| Compound 18 | <100 | 5600 | >56 |

Anti-SARS CoV IC$_{50}$ (nm): the concentration of a compound at which the Vero E6 cells treated with the compound and SARS-CoV showed 50% CPEs.
Vero E6 Cell Cytotoxicity CC$_{50}$ (nM): the concentration of a compound at which the Vero E6 cells treated with this compound showed 50% cytotoxicity
Selective Index: the ratio between CC$_{50}$ and IC$_{50}$.

Example 3

Inhibition of TGEV Viral Protein Production

Swine testicular (ST) cells were cultured in a 96-well plate in the presence or absence of a test compound (at 8 different concentrations) for 2 hours and then infected with TGEV at a MOI of 10. Six hours after TGEV infection, the ST cells were fixed with 80% acetone and subjected to an indirect immunofluorescent assay (IFA) to examine the levels of TGEV spike (S) and nucleocapsid (N) proteins. Briefly, the fixed cells were incubated with murine monoclonal antibodies specific to these two viral proteins for a sufficient period to allow binding of the antibodies to the viral proteins. After being washed with phosphate-buffered saline for three times, the cells were incubated with a fluorescein isothiocyanate-conjugated anti-mouse immunoglobulin antibody (ICN Pharmaceutical, INC, Cappell) for 60 min at room temperature. The cells were washed again with phosphate-buffered saline for three times, and the fluorescence intensities released from these cells were measured by a Wallac Victor II system (Packard, Inc.) at excitation and emission wavelengths 485 nm and 535 nm, respectively. The 50% effective concentration ($EC_{50}$) for inhibiting S and N protein expression of the test compound was determined based on the florescence intensity values thus measured. Alternatively, the fluorescence intensities were detected by fluorescence microscopy. More specifically, the fluorescent images produced under 485 nm and 535 nm were captured by a charge-coupled device linked to a Leica IM50 Image Manager.

Certain compounds were tested in the assay described above. All of these compounds showed $EC_{50}$ values below 50 μM. Among them, Compounds 1-6, 11-16, 18, 30, 31, 42, and 43 showed $EC_{50}$ values lower than 100 nM and Compounds 8, 20, 22, 24, 26, 29, and 32 had $EC_{50}$ values lower than 500 nM.

In sum, the results obtained from this study indicate that phenanthroidolizidine analogues described herein effectively inhibited production of TGEV viral proteins, thereby suppressing viral replication.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous to the compounds of this invention can be made and used to practice this invention. Thus, other embodiments are also within the claims.

What is claimed is:

1. A method for treating a coronavirus infection, comprising administering to a subject in need thereof an effective amount of a compound of Formula I, Formula I wherein n is 1, 2 or 3;

each of ==== and ====, independently, is a single bond or a double bond;

each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$, independently, is H, halogen, alkyl, aryl, cyclyl, heteroaryl, heterocyclyl, OH, alkoxy, carbonyloxy, or amino;

each of $R_{16}$ and $R_{17}$, independently, is H, halogen, alkyl, aryl, cyclyl, heteroaryl, heterocyclyl, OH, alkoxy, carbonyloxy, or amino, or $R_{16}$ and $R_{17}$ together are a single bond; and when ==== is a single bond, X is C=O or CR'R" and Y is N or $N^+ \rightarrow O^-$, and when ==== is a double bond, X is CR', Y is $N^+$, and a counterion coexists in the compound; each of R' and R", independently, being H, halo, alkyl, aryl, cyclyl, heteroaryl, heterocyclyl, OH, alkoxy, or amino, and the coronavirus infection is caused by human CoV 229E, transmissible gastroenteritis virus, bovine CoV, feline CoV, or severe acute respiratory syndrome-associated coronavirus.

2. The method of claim 1, wherein $R_{16}$ and $R_{17}$ together are a single bond.

3. The method of claim 2, wherein each of $R_{10}$, $R_{11}$, $R_{12}$, $R_{13}$, $R_{14}$, and $R_{15}$ is H.

4. The method of claim 3, wherein each of $R_1$, $R_5$ and $R_8$ is H.

5. The method of claim 4, wherein each of $R_6$ and $R_7$, independently, is OH or alkoxy.

6. The method of claim 5, wherein each of $R_2$ and $R_3$, independently, is OH or alkoxy.

7. The method of claim 2, wherein each of ==== and ==== is a single bond.

8. The method of claim 7, wherein $R_9$ is OH, alkoxy, or carbonyloxy.

9. The method of claim 8, wherein X is $CH_2$.

10. The method of claim 1, wherein each of $R_{16}$ and $R_{17}$ is H.

11. The method of claim 10, wherein each of $R_{10}$, $R_{11}$, $R_{12}$, $R_{13}$, $R_{14}$, and $R_{15}$ is H.

12. The method of claim 11, wherein each of $R_1$, $R_5$ and $R_8$ is H.

13. The method of claim 12, wherein each of $R_2$, $R_3$, $R_6$, and $R_7$ is OH or alkoxy.

14. The method of claim 1, wherein the compound has the formula
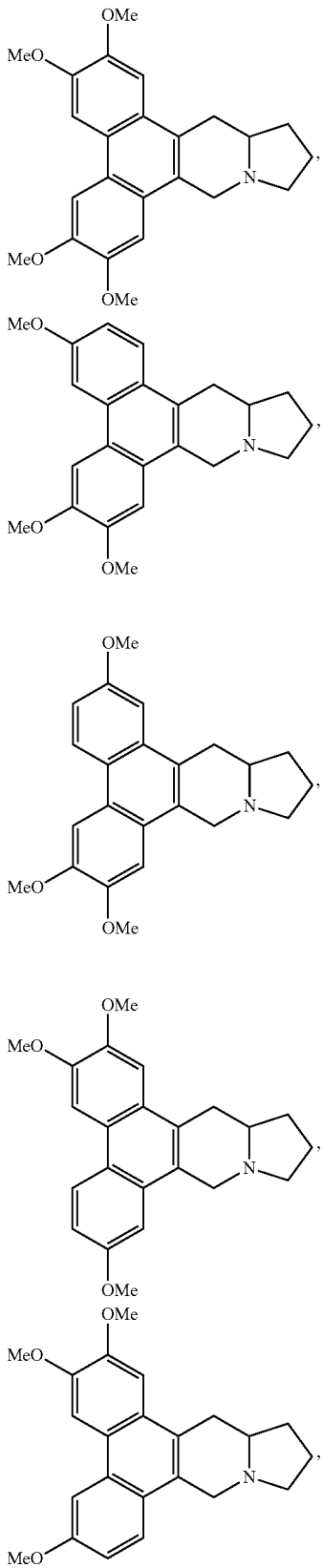
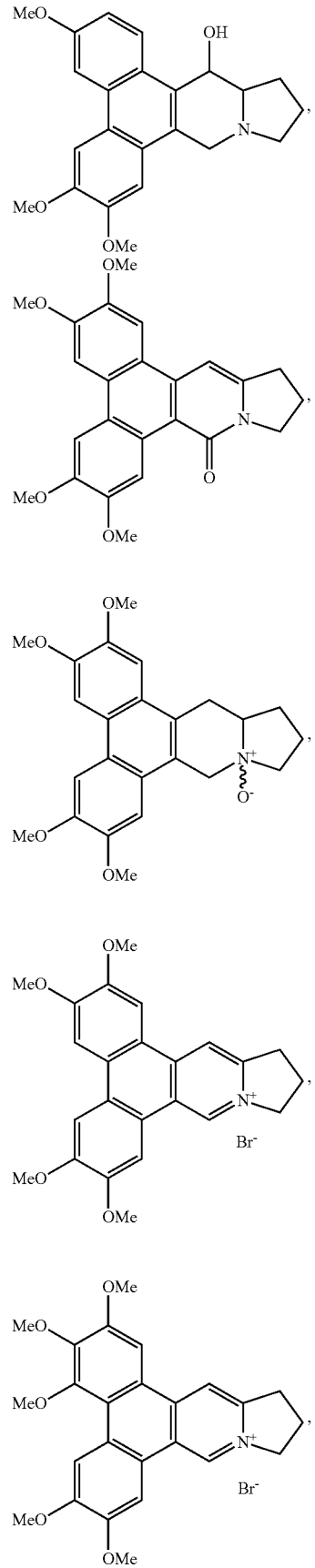

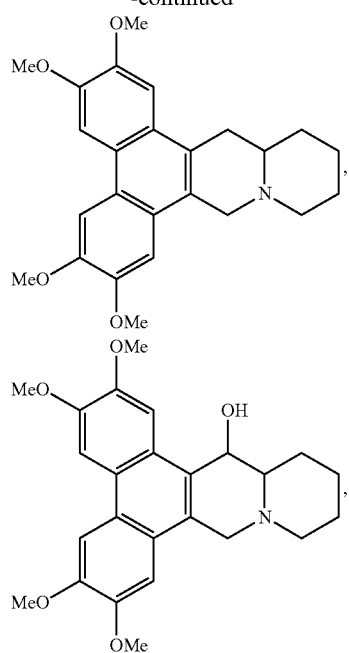
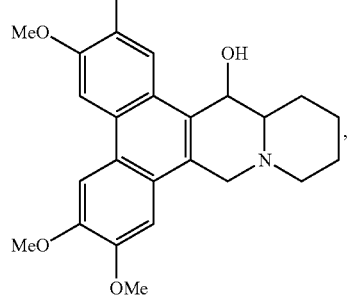
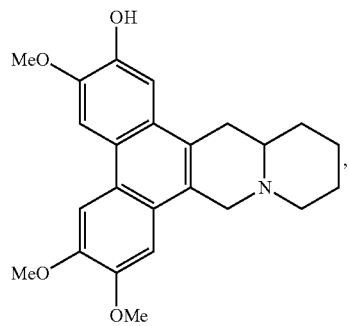
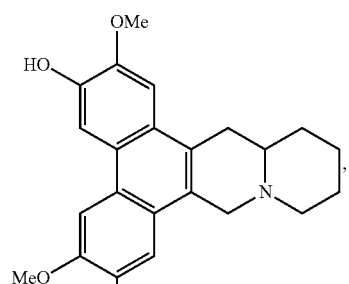
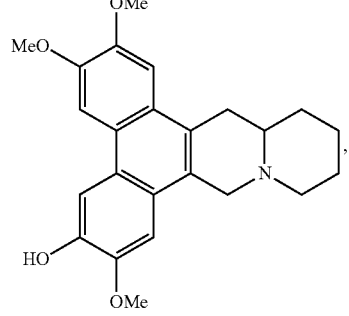
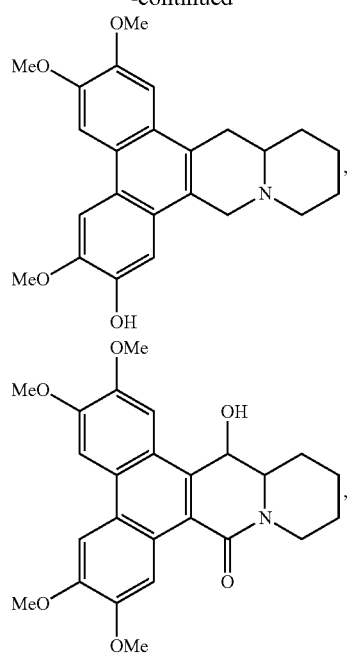
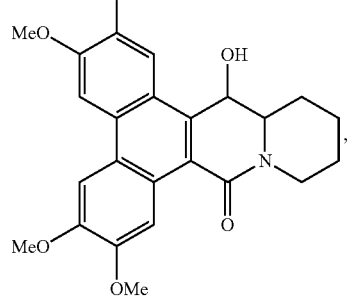
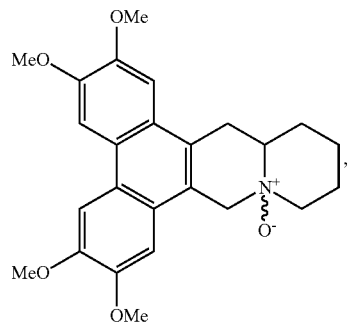
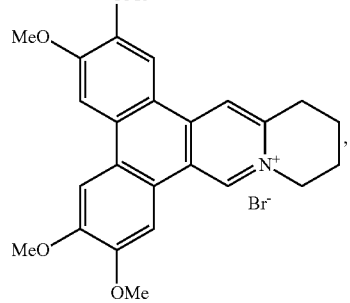
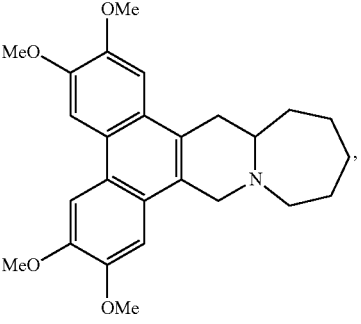

-continued

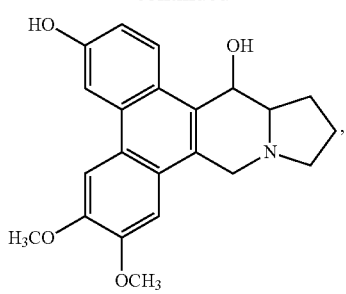
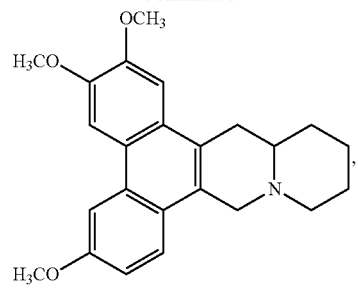
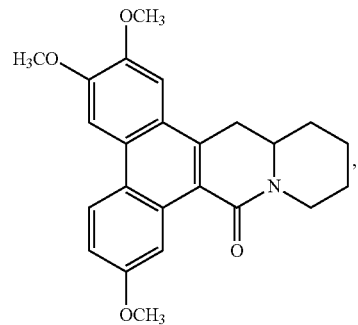
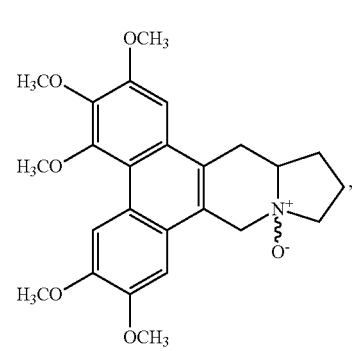
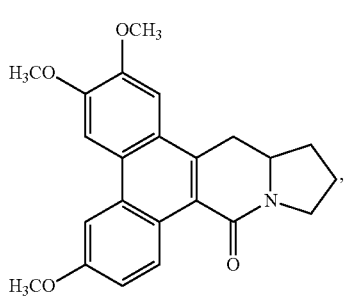
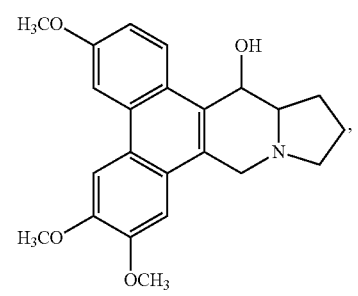
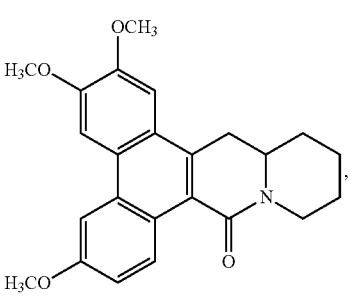
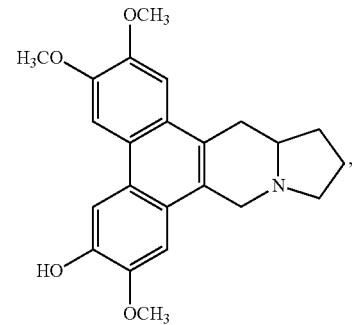

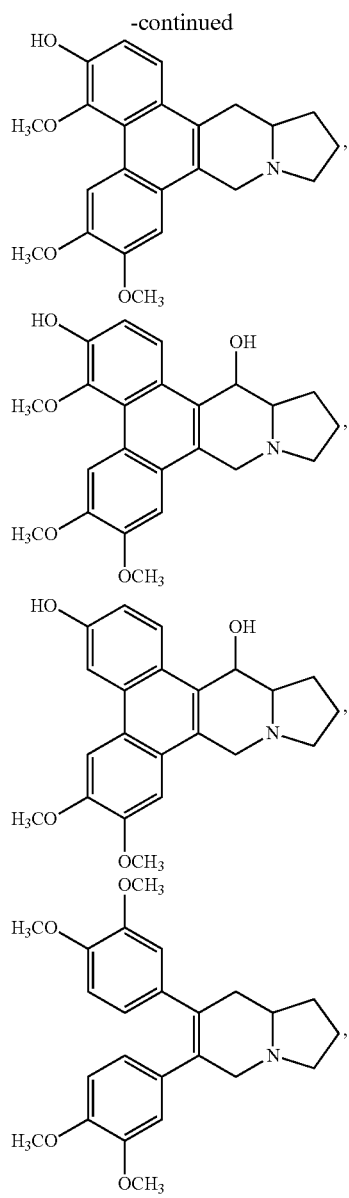
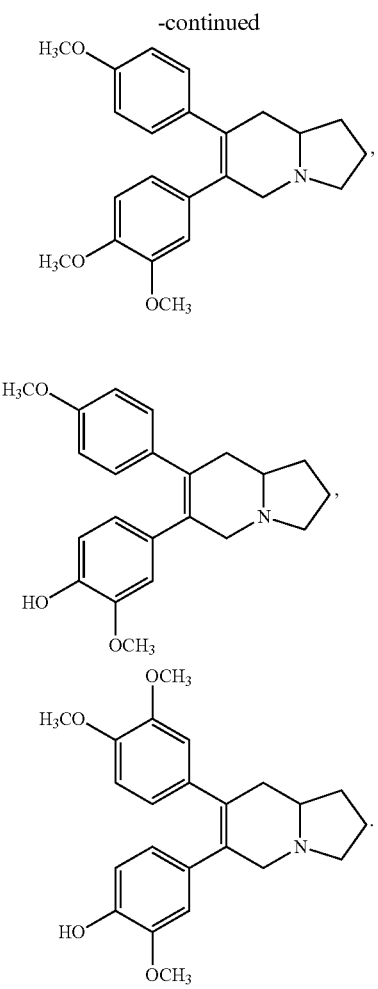
15. The method of claim 1, wherein the coronavirus infection is caused by, transmissible gastroenteritis virus, or severe acute respiratory syndrome-associated coronavirus.
16. The method of claim 15, wherein the coronavirus infection is caused by transmissible gastroenteritis virus.
* * * * *